(12) United States Patent
Fitzpatrick

(10) Patent No.: US 8,138,371 B2
(45) Date of Patent: Mar. 20, 2012

(54) PRODUCTION OF FORMIC ACID

(75) Inventor: Stephen W. Fitzpatrick, Framingham, MA (US)

(73) Assignee: Biofine Technologies LLC, Framingham, MA (US)

(*) Notice: Subject to any disclaimer, the term of this patent is extended or adjusted under 35 U.S.C. 154(b) by 0 days.

(21) Appl. No.: 12/401,987

(22) Filed: Mar. 11, 2009

(65) Prior Publication Data

US 2010/0234638 A1    Sep. 16, 2010

(51) Int. Cl.
C07C 51/00    (2006.01)
C07C 53/00    (2006.01)

(52) U.S. Cl. .................................. 562/515; 562/609

(58) Field of Classification Search ................. None
See application file for complete search history.

(56) References Cited

U.S. PATENT DOCUMENTS

| | | |
|---|---|---|
| 2,029,412 A | 2/1936 | Cox et al. |
| 3,959,509 A | 5/1976 | Evers et al. |
| 4,029,515 A | 6/1977 | Kiminki et al. |
| 4,228,278 A | 10/1980 | Shu et al. |
| 4,235,938 A | 11/1980 | Shu et al. |
| 4,236,021 A | 11/1980 | Hsu et al. |
| 4,326,073 A | 4/1982 | Wolf et al. |
| 4,470,851 A | 9/1984 | Paszner et al. |
| 4,529,699 A | 7/1985 | Gerez et al. |
| 4,897,497 A | 1/1990 | Fitzpatrick |
| 5,274,128 A | 12/1993 | Farbood et al. |
| 5,424,417 A | 6/1995 | Torget et al. |
| 5,503,996 A | 4/1996 | Torget et al. |
| 5,608,105 A | 3/1997 | Fitzpatrick |
| 5,705,369 A | 1/1998 | Torget et al. |
| 5,892,107 A | 4/1999 | Farone et al. |
| 6,054,611 A | 4/2000 | Farone et al. |
| 6,423,145 B1 | 7/2002 | Nguyen et al. |
| 6,660,506 B2 | 12/2003 | Nguyen et al. |
| 7,067,303 B1 | 6/2006 | Nichols et al. |
| 7,253,001 B2 | 8/2007 | Wahlbom et al. |
| 7,378,549 B2 | 5/2008 | Ayoub |
| 7,465,791 B1 | 12/2008 | Hallberg et al. |
| 7,501,062 B2 | 3/2009 | Den Boestert et al. |
| 2002/0148574 A1 | 10/2002 | Van Draanen et al. |
| 2003/0199049 A1 | 10/2003 | Nguyen et al. |
| 2004/0242924 A1 | 12/2004 | Zehner et al. |
| 2005/0153411 A1 | 7/2005 | Wahlbom et al. |
| 2006/0047139 A1 | 3/2006 | Ayoub |
| 2006/0140889 A1 | 6/2006 | Houtzager et al. |
| 2006/0201879 A1 | 9/2006 | Den Boestert et al. |
| 2006/0210500 A1 | 9/2006 | Bicard-Benhamou |
| 2006/0246149 A1 | 11/2006 | Bucholz et al. |
| 2007/0079944 A1 | 4/2007 | Amidon et al. |
| 2007/0100162 A1 | 5/2007 | Petrus et al. |
| 2007/0123577 A1 | 5/2007 | Miyata et al. |
| 2007/0161095 A1 | 7/2007 | Gurin |
| 2007/0190629 A1 | 8/2007 | Wahlbom et al. |
| 2008/0057555 A1 | 3/2008 | Nguyen |
| 2008/0176956 A1 | 7/2008 | Hsu |
| 2008/0295980 A1 | 12/2008 | Hallberg et al. |
| 2008/0299629 A1 | 12/2008 | Hallberg et al. |
| 2009/0004726 A1 | 1/2009 | Liu |
| 2009/0056889 A1 | 3/2009 | Ren et al. |
| 2009/0068255 A1 | 3/2009 | Yu et al. |
| 2009/0084025 A1 | 4/2009 | Bhatia et al. |
| 2009/0098616 A1 | 4/2009 | Burke et al. |
| 2009/0098617 A1 | 4/2009 | Burke et al. |
| 2009/0117226 A1 | 5/2009 | Hallberg et al. |
| 2009/0118477 A1 | 5/2009 | Hallberg et al. |

FOREIGN PATENT DOCUMENTS

| | | |
|---|---|---|
| WO | WO 89/10362 | 11/1989 |
| WO | WO 96/40609 | 12/1996 |

OTHER PUBLICATIONS

Lewkowski, ARKIVOC, Synthesis, Chemistry and Applications of 5-Hydroxymethyfurfural and its Derivatives, 2001, (i), pp. 17-54.*
Girisuta, B. et al., "A kinetic study on the decomposition of 5-hydroxymethylfurfural into levulinic acid", Green Chemistry, vol. 8, pp. 701-709, (2006).
Girisuta, B. et al., "Kinetic Study on the Acid-Catalyzed Hydrolysis of Cellulose to Levulinic Acid", American Chemical Society, pp. A-M, (2007).
Girisuta, B. et al., "Green Chemicals—A Kinetic Study on the Conversion of Glucose to Levulinic Acid", Trans IChemE, Part A, Chemical Engineering Research and Design, vol. 84(A5), pp. 339-349, (2006).

* cited by examiner

*Primary Examiner* — Paula A Zucker
(74) *Attorney, Agent, or Firm* — Fish & Richardson P.C.

(57) ABSTRACT

Processes for producing formic acid from a carbohydrate-containing material include hydrolyzing a carbohydrate-containing material (e.g., cellulose) in the presence of a mineral acid to form an intermediate hydrolysate comprising one or more sugars, and hydrolyzing the intermediate hydrolysate to form a hydrolysate product including formic acid.

29 Claims, 1 Drawing Sheet

PRODUCTION OF FORMIC ACID

TECHNICAL FIELD

This disclosure relates to the production of formic acid.

BACKGROUND

Many common materials consist partially or mostly of carbohydrate molecules, predominantly polymers of glucose, galactose, or similar hexose sugars. When subjected to acid treatment, carbohydrate molecules such as cellulose can be hydrolyzed to form hexose monomers and various other intermediate reaction products. With continued hydrolysis, the hexose monomers can further degrade to end products such as levulinic acid and formic acid. Formic acid can be further degraded to carbon monoxide. For example, formic acid can be degraded according to the following reaction:

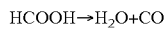

$HCOOH \rightarrow H_2O + CO$

As a result, the formic acid yield obtained from carbohydrate-containing materials by acid hydrolysis processes can be reduced.

Formic acid is a useful commodity chemical with many industrial applications. One conventional method for producing formic acid is from crude oil derived chemical intermediates. However, processes for producing formic acid from other sources would also be useful.

SUMMARY

The invention provides a process for producing formic acid in good yield from a carbohydrate-containing material. Generally, the carbohydrate-containing material (e.g., a feedstock containing cellulose) is converted to formic acid in multiple reactions: (1) acid hydrolysis of the carbohydrate-containing material to an intermediate hydrolysate containing one or more sugars (e.g., sugars produced by hydrolyzing glycosidic bonds in the cellulose feedstock); and (2) additional hydrolysis of the intermediate hydrolysate to a hydrolysate product containing formic acid. The processes can also include (3) isolating the formic acid from the hydrolysate product in a vapor form. The yield of formic acid based on carbohydrate can be, for example, greater than 55%, and preferably greater than about 70% of the theoretical yield.

The acid hydrolysis of the carbohydrate-containing material can be performed in an aqueous slurry with a mineral acid, such as sulfuric acid, at a temperature and pressure allowing formation of the intermediate hydrolysate. For example, the aqueous acid slurry of carbohydrate-containing feedstock material can be hydrolyzed for about 10 to 60 seconds at a temperature of about 195 to 235 degrees C. to form the intermediate hydrolysate. The subsequent hydrolysis of the intermediate hydrolysate can be performed under conditions that avoid undesirable of formic acid degradation. In one example, the hydrolysis of the intermediate hydrolysate can be performed at a temperature less than 195 degrees C. and a pressure effective to form a hydrolysate product comprising formic acid in high yield. In another example, the hydrolysis of the intermediate hydrolysate can be performed at a temperature of 150 to 210 degrees C. and a pressure effective to form a hydrolysate product comprising formic acid and levulinic acid in an amount that provides a molar ratio of the levulinic acid to the formic acid of at least 0.9 in a hydrolysate product. In a third example, the hydrolysis of the intermediate hydrolysate can be performed using mineral acid in an amount of 3.0 to 4.5 wt of the hydrolysate liquid material.

Systems for producing formic acid from carbohydrate-containing material can include a first reactor adapted to perform an initial hydrolysis of the carbohydrate-containing material, and a second reactor adapted to perform a subsequent hydrolysis of the intermediate hydrolysate received from the first reactor to form the hydrolysate product. The system can include vessels for separately collecting vapor and liquid phases containing formic acid from the second reactor, as well as equipment for condensing formic acid from the vapor phase of the hydrolysate product.

DETAILED DESCRIPTION

Figure 1:
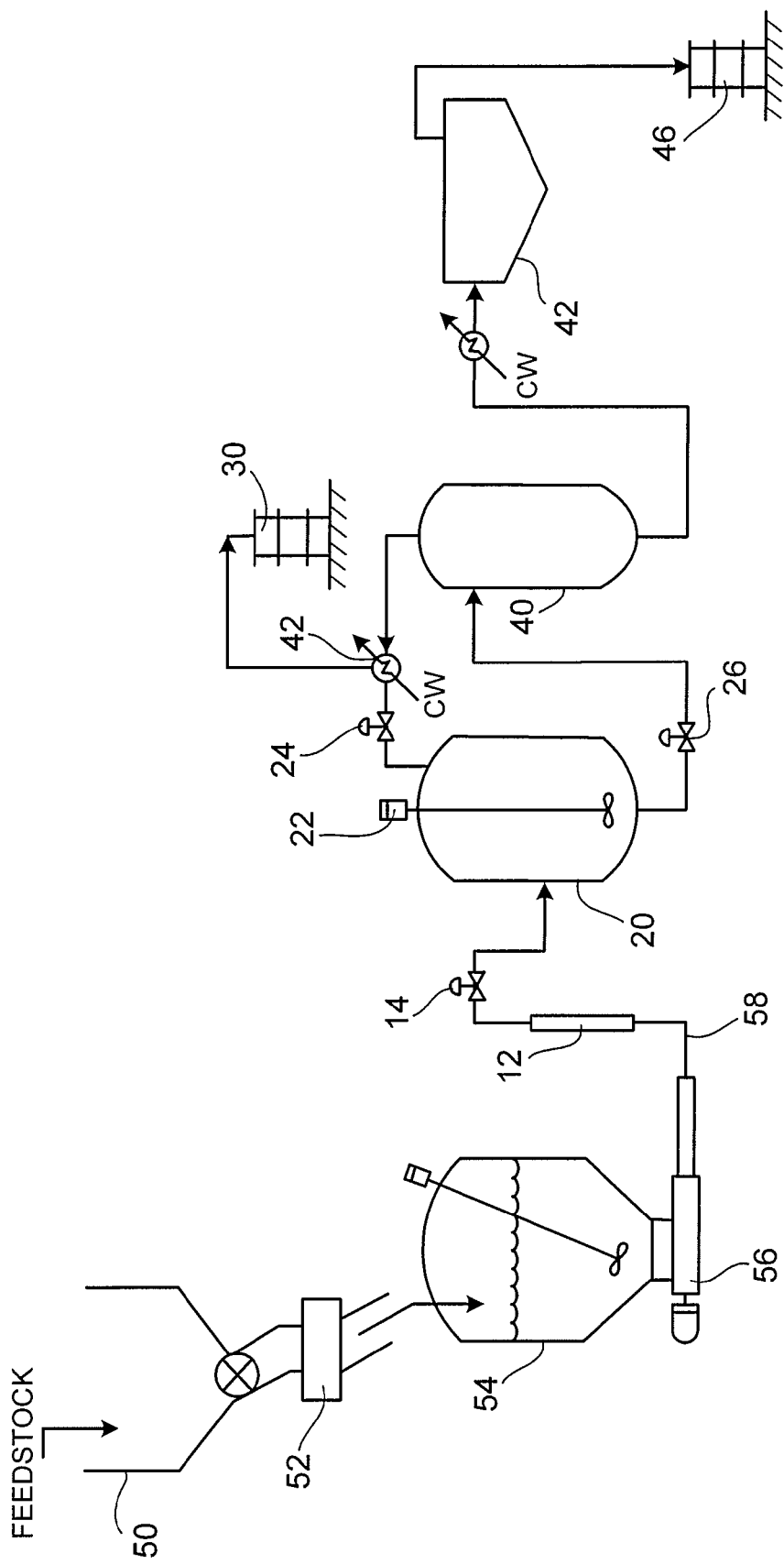
FIG. 1 is a schematic diagram of a system for producing formic acid from a carbohydrate-containing material.

Referring to FIG. 1, a system 10 for producing formic acid can include a first reactor 12, shown as a tubular reactor, adapted to hydrolyze a carbohydrate-containing material in an acid to form an intermediate hydrolysate containing one or more sugars. The first reactor 12 is connected to a second reactor 20 adapted to hydrolyze the intermediate hydrolysate to form a hydrolysate product containing formic acid. The second reactor 20 is connected to a flash tank 40 to separate formic acid as a vapor from the hydrolysate product. Conditions in the first reactor 12 and the second reactor 20 can be controlled to obtain desired yields of formic acid from the hydrolysate product, for example by reducing or minimizing the degradation of formic acid. Unless otherwise indicated, the terms "first reactor" and "second reactor" refer to equipment suitable for hydrolyzing the carbohydrate-containing material and the intermediate hydrolysate, respectively. In system 10, the second reactor 20 is configured as a second stage reactor vessel including a mixer 22 configured to back mix the contents of the second reactor 20. In other examples of systems suitable for performing the methods described herein, the first reactor 12 and second reactor 20 can have configurations that differ from those shown in the system 10. For example, the first reactor 12 and the second reactor 20 can instead be configured as portions of a single reactor vessel that are configured to perform the hydrolysis of the carbohydrate-containing material in a first portion forming the first reactor and hydrolysis of the intermediate hydrolysate in a second portion forming the second reactor.

The carbohydrate-containing material can be supplied to the first reactor 12 as an aqueous acid slurry. The carbohydrate-containing material can contain or consist essentially of polymers of sugars (e.g., materials comprising or consisting essentially of cellulose and/or hemicellulose). Examples of carbohydrate-containing materials include wood, paper pulp, waste paper sludge, waste paper, food waste, straw, switchgrass and the like. In the system 10, a feedstock material including the carbohydrate-containing material is introduced to a feeder 50 (e.g., a weigh hopper). The feedstock can be passed through a grinder 52 between the feeder 50 and the mixer 54. The feedstock is fed from the feeder 50 to a mixer 54, where it is mixed with an acid to form an aqueous slurry that is pumped into the first reactor 12.

The amount of solid in the aqueous slurry formed in the mixer 54 can be selected to provide a slurry that can be transported by the high pressure pump 56 through the steam injection section 58 and into the first reactor 12. For example, the aqueous slurry in the mixer 54 can include up to about 20% wt of solid feedstock material, including an aqueous slurry having about 1-20% wt., such as 10% wt of the cellulose-containing material. The amount of a solid feedstock material in the aqueous slurry can be selected based on the capacity of the system 10 to pump the slurry through the first reactor 12 and other components of the system 10.

The feedstock is mixed with an acid as an aqueous slurry in the mixer 54. The acid concentration in the aqueous slurry can be high enough to provide a desired hydrolysis reaction rate and/or degree of hydrolysis of the carbohydrate-containing material, but low enough to prevent undesired corrosion of a reactor system. The acid can be a mineral (e.g., inorganic) acid, such as hydrochloric acid, nitric acid, phosphoric acid, sulfuric acid, hydrofluoric acid, hydrobromic acid and the like. For example, an aqueous slurry of cellulose-containing material can have a mineral acid concentration of about 1 to 10% wt, including concentrations of about 1 to 6% wt, 2 to 5% wt, and 3 to 4.5% wt. The carbohydrate-containing material can be a pulverized or macerated solid (e.g., wood pulp) in a form suitable for combination with a dilute acid to form an aqueous slurry. The acid and acid concentration in the aqueous slurry is selected to hydrolyze the carbohydrate-containing material at a desired concentration and reactor conditions. For example, an aqueous slurry containing about 1-10% wt sulfuric acid can be formed in the mixer 54 and pumped into the first reactor 12. The aqueous acid slurry containing the carbohydrate-containing material can be pumped from the mixer 54 into the first reactor 12 using the high pressure pump 56 through a steam injection section 58 and into the first reactor 12, shown as a tubular reactor.

The carbohydrate-containing material in the aqueous acidic slurry can be hydrolyzed to form the intermediate hydrolysate in the first reactor 12. The first reactor 12 is shown as a continuous flow tubular reactor configured to minimize axial mixing. The aqueous acid slurry containing the carbohydrate-containing material flows through the tubular reactor. The pressure of the aqueous slurry in the tubular reactor can be high enough to maintain the aqueous slurry above the boiling point (i.e., the saturated pressure) to maintain the contents of the tubular reactor in a fluid form, but low enough to prevent damage to the system 10. The aqueous slurry formed in the mixer 54 and pumped into the tubular reactor can have a mineral acid concentration of about 1-10% wt, 2-5% wt, or 3-4.5% wt. of the contents of the first reactor 12.

The hydrolysis of the carbohydrate-containing material can be performed in the first reactor 12 at a temperature and pressure, and for a time period, effective to provide a desired amount of hydrolysis products in the intermediate hydrolysate. The intermediate hydrolysate can include a mixture of various sugars, such as hexose sugars (e.g., obtained by hydrolyzing glycosidic bonds between sugars in a cellulose or hemicellulose material in the acid slurry). The carbohydrate-containing material can be hydrolyzed to form an intermediate hydrolysate containing glucose, and other sugars such as xylose, mannose, galactose, rhamnose, and arabinose. Other substances such as hydroxymethylfurfural (HMF) can also be present in the intermediate hydrolysate. Conditions in the first reactor 12 that can be adjusted to hydrolyze the carbohydrate-containing material include: (a) the temperature and pressure of the carbohydrate-containing material in the first reactor 12, (b) the acid concentration in the first reactor 12 and (c) the period of time the carbohydrate-containing material spends in the first reactor 12 ("residence time"). These variables can be chosen to reduce or minimize the degradation of any formic acid formed in the first reactor 12 to carbon monoxide (CO). The carbohydrate-containing material in an aqueous acidic slurry can be heated to, or maintained at, a first temperature within the first reactor 12 that is high enough to permit hydrolysis of at least a portion of the material into one or more sugars, and low enough to prevent deposition of carbonaceous material (e.g., "coke") inside the reactor and/or degradation of formic acid. For example, the aqueous slurry of cellulose-containing carbohydrate material can be about 150 to 235 degrees C. within the first reactor 12 (including, for example, temperatures of up to about 210 degrees C., about 150 to 210, 150 to 205, 150 to 180, 150 to 175, 175 to 235, 175 to 210, 175 to 205, 175 to 180, 195 to 235, 195 to 220, 195 to 210, 195 to 205 degrees C.). The rate of fluid flow of the carbohydrate-containing material through the first reactor 12 can be selected to provide a residence time within the first reactor 12 of up to about 60 seconds, preferably a first residence time of about 10-60 seconds.

The carbohydrate-containing material is hydrolyzed in the first reactor 12 until a desired amount of intermediate hydrolysate is formed in the first reactor 12. In the system 10 shown in FIG. 1, the residence time of the acidic carbohydrate-containing aqueous slurry in the tubular first reactor 12 can be adjusted by using other reactors with different dimensions (or, by varying the rate of the feed pump 56). In one example, the carbohydrate-containing material is hydrolyzed with about 2-5% mineral acid in an aqueous slurry for 10 to 60 seconds at a first temperature of about 190 to 205 degrees C. to produce the intermediate hydrolysate in the first reactor 12. The carbohydrate-containing material can be hydrolyzed in the first reactor 12 with about 2-5% wt mineral acid for a residence time of about 10 to 60 seconds at a temperature of about 190 to 205 degrees C., and a pressure effective to maintain the contents of the first reactor 12, including the intermediate hydrolysate, as a fluid within the first reactor 12. In another example, a cellulose-containing material is supplied continuously from the mixer 54 to the first reactor 12, where the cellulose-containing material is hydrolyzed at between 200 degrees Centigrade and 225 degrees Centigrade for between 13 and 35 seconds in the presence of between 3% and 6% by weight mineral acid. The hydrolysis in the first reactor 12 can produce an intermediate hydrolysate containing hydroxymethylfurfural, glucose and glucose oligomers.

The intermediate hydrolysate can be transferred from the first reactor 12 to the second reactor 20 in a continuous or batch process. In the system 10, the intermediate hydrolysate is continuously removed from the tubular first reactor 12 and forced (e.g., under pressure) through a first pressure control valve 14 into the second reactor 20, although other configurations can include a batch reactor instead of the continuous flow tubular reactor. The first pressure control valve 14 can maintain the second reactor 20 at a lower pressure than the first reactor 12. The intermediate hydrolysate can flow continuously from the tubular reactor through the first pressure control valve 14 into the second reactor 20 equipped with an agitator 22 to ensure that it is completely mixed.

Within the second reactor 20, the intermediate hydrolysate can be further hydrolyzed to form a hydrolysate product. The temperature, pressure and residence time of the intermediate hydrolysate within the second reactor 20 can be selected to provide a desired amount and degree of hydrolysis of the components of the intermediate hydrolysate. Preferably, the hydrolysis of the intermediate hydrolysate is performed under conditions effective to produce formic acid (although formic acid can also be produced during the initial hydrolysis of the carbohydrate-containing material). Conditions during the hydrolysis of the intermediate hydrolysate can be selected to minimize the amount of sugars, such as glucose, remaining in the hydrolysate product. The temperature during the hydrolysis of the intermediate hydrolysate can be high enough to permit hydrolysis of the intermediate hydrolysate to form desired products at a desired rate, but not high enough to degrade a desired product such as formic acid (e.g., by converting formic acid to CO and water), or result in the undesired generation of solid amorphous carbonaceous material (e.g., "coking" or "coke" deposition in a reactor). In general, the temperature and pressure in the second reactor 20 are also selected to maintain the intermediate hydrolysate in a fluid form, which can include a vapor phase and a liquid phase within the second reactor 20.

For example, an intermediate hydrolysate containing glucose, glucose oligomers, HMF and other sugars can be maintained for a residence time in the second reactor 20 at a temperature and pressure effective to form a mixture of formic acid and levulinic acid, without undesired levels of formic acid degradation to form CO and water. When a cellulose-containing feedstock is used, the temperature, pressure and residence time of the intermediate hydrolysate in the second reactor 20 can also be selected to minimize the amount of glucose remaining in the hydrolysate product. For formic acid production, the temperature in the second reactor 20 can be maintained at about 150 to 210 degrees C. (e.g., including temperatures of about 150 to 195 degrees C.), with the pressure determined by the configuration of the second reactor 20. The second reactor 20 can operate at the saturated pressure of the reaction mixture which can be between 5 and 14 bar gauge. The residence time of the intermediate hydrolysate in the second reactor 20 can be, for example, about 10 to 60 minutes at these temperature and pressures. Accordingly, formic acid can be produced at a yield of least 55% and more preferably 70% or more of the theoretical yield based on the hexose-containing content of the carbohydrate-containing material in the feedstock. In system 10, the second reactor 20 is a second stage reactor including an agitator 22 that continuously stirs the contents of the second reactor 20. In one example, hydroxymethylfurfural in the hydrolysate intermediate is hydrolyzed further in the second reactor 20 at between 160 degrees centigrade and 195 degrees Centigrade for between 10 and 60 minutes to produce formic acid which is continuously removed from the second reactor 20.

Formic acid can be isolated from the hydrolysate product. The second reactor 20 of system 10 is configured to contain the hydrolysate intermediate and/or the hydrolysate product in a liquid phase and/or a vapor phase. Portions of the hydrolysate product, such as formic acid, can be isolated in both the vapor phase and the liquid phase from the second reactor 20. By performing the hydrolysis of the intermediate hydrolysate at a lower pressure than the initial hydrolysis of the carbohydrate-containing material, formic acid can be obtained in a vapor phase. The second reactor 20 can be maintained at a lower pressure than the first reactor 12, permitting at least some portion of the fluid hydrolysate intermediate from the first reactor 12 to form a vapor phase within the second reactor 20. The temperature and pressure in the second reactor 20 can be selected to form a hydrolysate product partially in the vapor phase and partially in a liquid phase.

Formic acid can be separated as a vapor from a liquid portion of the hydrolysate product from the second reactor 20 (e.g., by condensation). The vapor phase within the second reactor 20 can include formic acid formed in the first reactor 12 and/or formic acid formed in the second reactor 20. Vapor containing formic acid can evaporate within the second reactor 20. The second reactor 20 can include an opening for removing the vapor phase, from which formic acid can be subsequently condensed. The vapor from the second reactor 20 passes through control valve 42 is condensed and is collected in the condensate collection tank 30.

The remaining liquid contents of the second reactor 20 can also contain formic acid that has not evaporated. The liquid portion of the hydrolysate product can be vaporized, for example by flashing, to separate additional quantities of vapor phase formic acid. The second reactor 20 can include an opening for removing the liquid phase, which can be flashed into a separate vessel at a lower pressure than the second reactor to form a second vapor phase. The liquid phase of the hydrolysate product can leave the second reactor 20 through a level control valve 26. The liquid leaving the second reactor 20 through the level control valve 26 flows to a flash tank 40 maintained at a lower pressure than the second reactor 20. The lower pressure in the flash tank 40 allows the volatile formic acid to boil off as a vapor affording yet another opportunity to recover vapors containing formic acid remaining in the hydrolysate product in the second reactor 20. Again, volatile products such as formic acid can be collected from the flash tank 40, and subsequently condensed to isolate formic acid from the liquid phase of the second reactor 20. The flash tank 40 may optionally include internal shelves or trays and a source of heat such as a tank jacket, reboiler or steam injector to promote increased recovery of formic acid in the vapor phase. The pressure in the second reactor 20 allows the hydrolysate product to flow out under level control into the flash tank 40, held at a lower pressure than the second reactor 20. In the flash tank 40, additional vapor containing formic acid evaporates due to the reduction in pressure. This vapor is condensed and collected in the condensate collection tank 30. The quantity of formic acid collected in the condensate collection tank 30 is recorded. Any non-volatile liquid remaining in the flash tank 40 can be removed from the flash tank 40. Additional products can be separated from the remaining liquid phase in the flash tank 40 and/or a second reactor 20, for example by distillation or spraying into additional flash vessels of progressively lower pressures.

Formic acid can be obtained in an amount of about 2.0-2.5% wt of the liquid condensate product from the second reactor 20, and about 50% wt of the formic acid produced according to the processes described herein can be obtained from the liquid hydrolysate product. For example, about half of the formic acid can be obtained from the vapor phase in the second reactor 20 (i.e., as a liquid condensate product), with the remaining amount of formic acid obtained from liquid hydrolysate product. Increasing the temperature in the second reactor 20 can increase the relative amount of formic acid present in the vapor phase relative to the liquid hydrolysate product in the second reactor 20. The total quantity of formic acid produced by the hydrolysis reaction during a certain period of operation can be the sum of formic acid in the liquids collected in the condensate tank 30, settler tank 42 and overflow tank 46 during the same period of operation. The quantity of formic acid in the condensate collection tank 30 can be calculated by multiplying the fraction of formic acid in the condensate from the condensate collection tank 30 by the quantity of condensate that has been collected in the condensate collection tank 30. The fraction of formic acid in any liquid from a tank can be measured by analysis of a sample of the liquid in the tank using a validated analytical technique such as high pressure liquid chromatography or HPLC. For example, the quantity of formic acid in the settler tank 42 can be calculated by multiplying the fraction of formic acid in the settler tank 42 liquid by the change in the quantity of liquid in the settler tank 42 as measured by the level in the settler tank 42. The quantity of formic acid in the overflow tank 46 can be calculated by multiplying the fraction of formic acid in the liquid in the overflow tank 46 by the change in the quantity of liquid in the overflow tank 46, as measured by the tank level change during the period of operation of the system 10.

In system 10, the residual liquid from the low pressure tank is pumped through a control valve 44 into a solids settler tank 42. The quantity of liquid in the solids settler tank 42 can be recorded by measuring the tank level. The overflow from the solids settler tank 42 flows to an overflow tank 46. The quantity of liquid collected in the overflow tank 46 can be recorded by measuring the tank level.

Optionally, the formic acid in the liquid phase obtained from the second reactor 20 can be recycled within the reactor system 10, and can be eventually removed from the system 10 as a vapor from either the second reactor 20 or lower pressure downstream equipment such as the flash tank 40. For example, recycle acid hydrolysate can be added to the carbohydrate-containing material in the feeder 50, the mixer 54, or via a grinder 52 positioned between the feeder 50 and the mixer 54 as shown in FIG. 1.

The amount of carbon monoxide in the vapor phase in the second reactor 20 can be monitored during the formic acid production process. Conditions such as temperature, pressure and residence time in the second reactor 20 can be adjusted to minimize the concentration of carbon monoxide (a degradation product of formic acid) in the second reactor 20. For example, the temperature in the second reactor 20 can be lowered in response to increasing levels of carbon monoxide in the vapor phase in the second reactor 20.

Unless otherwise stated, the yield of formic acid from a cellulose carbohydrate-containing material is calculated by dividing the quantity of cellulose fed to the hydrolysis reactor in a measured time by the quantity of formic acid collected in the same time period as described above. The quantity of cellulose fed is equal to the quantity of feedstock fed to the reactor multiplied by the fraction of cellulose measured in the feedstock. The cellulose fraction measured in the feedstock is the total hexose sugar-containing fraction in the feedstock as measured by a validate procedure.

EXAMPLES

The invention is further described in the following examples. Exemplary methods of making formic acid are described below.

Processes for producing formic acid from a carbohydrate-containing material in high yields were performed using a system illustrated in FIG. 1, including two reactors in which the temperature, reaction time and acid content are closely controlled. When the temperature of the second reactor was greater than 195 degrees Centigrade, high yields of levulinic acid were obtained but the yield of formic acid was much lower than expected. Table 1 shows results from such experiments. A molar yield ratio of levulinic acid to formic acid of 1.0 would be theoretically obtained.

However, as the data in Table 1 indicates, the molar yield ratio of formic acid to levulinic acid obtained can be increased by decreasing the second stage reactor temperature and increasing the hydrolysate acid concentration. More specifically, the data in Tables 1 and 2 indicate that operating the second stage reactor in the range 170 deg. C. to 193.3 deg. C. and increasing the hydrolysate acid concentration into the range 3.0% to 4.5% result in mole ratios of formic acid to levulinic acid in the range 0.89 to 1.2. By comparison, operation of the second stage reactor at 200 deg. C. to 205 deg. C. and lower acidity in the range 1.5% to 2.0% leads to a much lower range of molar ratio between 0.24 and 0.54.

TABLE 1

| PFR Temp. Deg. C. (reactor 1) | CSTR Temp. Deg. C. (reactor 2) | Acid conc. % wt | Residence time in PFR (sec.) (reactor 1) | Residence time in CSTR (min.) (reactor 2) | Molar ratio levulinic acid to formic acid |
|---|---|---|---|---|---|
| 215 | 200 | 1.5% | 21 | 20 | 0.242 |
| 215 | 200 | 1.5% | 21 | 20 | 0.300 |
| 215 | 205 | 1.5% | 21 | 20 | 0.415 |
| 220 | 200 | 2.0% | 18 | 12 | 0.365 |
| 220 | 200 | 2.0% | 21 | 14 | 0.523 |
| 218 | 201 | 1.5% | 20 | 17 | 0.542 |

However, when the temperature of the second stage reaction was maintained below 195 degrees Centigrade, the yield of formic acid increased significantly. In addition, when the acidity was increased above 3%, then the yield of levulinic acid was also maintained at a high level (around 70% of theoretical). These results are shown in Table 2.

TABLE 2

| PFR Temp. Deg. C. (reactor 1) | CSTR Temp. Deg. C. (reactor 2) | Acid conc. % wt | Residence time in PFR (sec.) (reactor 1) | Residence time in CSTR (min.) (reactor 2) | Molar ratio levulinic acid to formic acid |
|---|---|---|---|---|---|
| 210 | 185 | 4.0 | 30 | 27 | 1.20 |
| 205 | 185 | 4.0 | 15 | 25 | 0.926 |
| 205 | 170 | 4.5 | 20 | 35 | 1.01 |
| 205 | 170 | 4.5 | 20 | 35 | 1.04 |
| 220 | 193 | 3.0 | 12 | 20 | 0.89 |
| 220 | 193.3 | 3.0 | 12 | 20 | 1.07 |

As evidenced by the data in Table 1 and Table 2, it is clear that a combination of lower temperature in the second reactor and higher acidity in the reaction maintained the molar ratio of formic acid to levulinic acid at around 1.0. Thus at these conditions, it is possible to avoid breakdown of the formic acid while maintaining high yield of levulinic acid.

The following examples were obtained from the operation of a semi-commercial scale pilot plant designed to incorporate the present invention. Three different types of feedstock were used:

1. A mixed hardwood and softwood feed with an average composition as follows:

| | |
|---|---|
| Cellulose: | 21.8% |
| Hemicellulose: | 15.1% |
| Lignin: | 13.0% |
| Ash/others: | 2.1% |
| Moisture: | 48% |

2. A crude paper pulp feed with an average composition as follows:

| | |
|---|---|
| Cellulose: | 70.1% |
| Hemicellulose: | 20.9% |
| Water: | 9.0% |

3. A waste paper sludge with an average composition as follows:

| | |
|---|---|
| Cellulose | 50.6% |
| Hemicellulose/others | 32.8% |
| Ash | 11.7 |
| Water | 4.9% |

All chemical analyses for both feedstock and the plant streams were measured by validated methods. The cellulose fraction pertains to polymeric hexose sugar chains. The hemicellulose pertains to polymeric pentose sugar chains. The plant has an automatic feed metering system to measure feedstock added. The description of the plant has been provided previously in this disclosure.

Example 1

Mixed Hardwood and Softwood Feedstock

In the pilot plant operation a wood sawdust stream containing wood particles of around 2 mm on average were fed to the pilot plant process. The total quantity of wood fed was 165.6 Kilograms. The cellulose content of this wood was measured at 36.2 Kilograms (See above analysis for wood). Dilute formic acid was obtained as a condensate stream and the formic acid content of the resulting liquid streams was also measured. Formic acid produced in the condensate streams was estimated to be 4.8 kilograms and formic acid produced in the liquid streams was measured to be 2.5 Kg. The total production of formic acid in this operation was 7.3 Kg. The yield of formic acid from cellulose was therefore 7.3 divided by 36.2 or 20.2%. The maximum theoretical yield of formic acid from cellulose is 27.3%. The yield obtained therefore represents 74% of theoretical yield. In this experiment the yield of levulinic acid was 40% by weight % and the molar ratio was 1.20

The reaction conditions for this operation were as follows:

| | |
|---|---|
| First stage reaction temperature: | 210 degree Celsius |
| First stage reaction residence time: | 30 seconds |
| First stage reactor diameter: | 5 cm |
| Second stage reactor temperature: | 185 degrees Celsius |
| Second stage reaction residence time: | 27 minutes |
| Acid concentration reaction liquor: | 4% by weight |

Example 2

Paper Pulp Feedstock

In the pilot plant operation a crude paper pulp stream containing ground paper was fed to the pilot plant process. The total quantity of pulp fed was 212.4 kilograms containing 148.8 kilograms of cellulose. Dilute formic acid was obtained in the condensate stream and the liquid streams was also measured. Formic acid produced in the condensate stream was measured to be 4.0 kilograms and formic acid produced in the liquid streams was measured to be 29.3 Kg. The total production of formic acid in this operation was 33.3 Kg. The yield of formic acid from cellulose was therefore 33.3 divided by 148.8 or 22%. The maximum theoretical yield of formic acid from cellulose is 27.3%. The yield obtained therefore represents 82% of theoretical yield. In this experiment the yield of levulinic acid was 61% by weight % and the molar ratio was 0.926.

The reaction conditions for this operation were as follows:

| | |
|---|---|
| First stage reaction temperature: | 205 degree C. |
| First stage reaction residence time: | 15 seconds |
| First stage reactor diameter: | 3.75 cm |
| Second stage reactor temperature: | 185 degrees C. |
| Second stage reaction residence time: | 25 minutes |
| Acid concentration reaction liquor: | 4% by weight |

Example 3

During one period of the pilot plant operation the pilot plant operation a crude paper pulp stream containing ground paper was fed to the pilot plant process. The total quantity of pulp fed was 661.5 kilograms containing 458.9 kilograms of cellulose. Dilute formic acid was obtained in the condensate stream and in the liquid streams. The total production of formic acid in this operation was 86.9 Kg as measured in the condensate and in the process tanks. The yield of formic acid from cellulose was therefore 86.9 divided by 458.9 or 18.93%. The maximum theoretical yield of formic acid from cellulose is 27.3%. The yield obtained therefore represents 69.3% of theoretical yield. In this experiment the yield of levulinic acid was 47% by weight % and the molar ratio was 1.01.

The reaction conditions for this operation were as follows:

| | |
|---|---|
| First stage reaction temperature: | 205 degree C. |
| First stage reaction residence time: | 20 seconds |
| First stage reactor diameter: | 5 cm |
| Second stage reactor temperature: | 170 degrees C. |
| Second stage reaction residence time: | 35 minutes |
| Acid concentration reaction liquor: | 4.5% by weight |

Example 4

During an extended period of the pilot plant operation the pilot plant operation lasting 288 hours a crude paper pulp stream containing ground paper was fed to the pilot plant process. The total quantity of pulp fed was 3,349.2 kilograms containing 2323.6 kilograms of cellulose. Dilute formic acid was obtained in the condensate stream and in the liquid streams. Total formic acid collected in the condensate stream was measured to be 192 kilograms and formic acid collected in the settler was calculated to be 220 Kg and formic acid collected in the overflow tank was calculated to be 26.8 Kg. The initial quantity of formic acid in the system prior to the production run was 4.5 Kg. Therefore, the total net production of formic acid in this operation was 434.8 Kg. The yield of formic acid from cellulose was therefore 434.8 divided by 2323.6 or 18.71%. The maximum theoretical yield of formic acid from cellulose is 27.3%. The yield obtained therefore represents 68.5% of theoretical yield. In this experiment the yield of levulinic acid was 46% by weight % and the molar ratio was 1.02.

The reaction conditions for this operation were as follows:

| | |
|---|---|
| First stage reaction temperature: | 205 degree C. |
| First stage reaction residence time: | 20 seconds |
| First stage reactor diameter: | 5 cm |
| Second stage reactor temperature: | 170 degrees C. |
| Second stage reaction residence time: | 35 minutes |
| Acid concentration reaction liquor: | 4.5% by weight |

Example 5

During one period of a pilot plant operation the pilot plant operation a crude paper sludge stream containing waste ground paper fiber was fed to the pilot plant process. The total quantity of paper sludge fed was 2102 kilograms containing 1063 kilograms of cellulose by analysis. Dilute formic acid was obtained in the condensate stream and in the liquid streams. The total production of formic acid in this operation was 163 Kg as measured in the condensate and in the process tanks. The yield of formic acid from cellulose was therefore 163 divided by 1063 or 15.3%. The maximum theoretical yield of formic acid from cellulose is 27.3%. The yield obtained therefore represents 56% of theoretical yield. In this experiment the yield of levulinic acid was 44.9% by weight % and the molar ratio was 0.89

The reaction conditions for this operation were as follows:

| | |
|---|---|
| First stage reaction temperature: | 220 degree C. |
| First stage reaction residence time: | 12 seconds |
| First stage reactor diameter: | 3.75 cm |
| Second stage reactor temperature: | 193 degrees C. |
| Second stage reaction residence time: | 20 minutes |
| Acid concentration reaction liquor: | 3% by weight |

This disclosure enables one skilled in the art to make and use other embodiments of the invention, including variations and combinations of exemplary processes and systems disclosed herein. Unless otherwise defined, all technical and scientific terms used herein have the same meaning as commonly understood by one of ordinary skills in the art to which this invention belongs. Unless otherwise indicated, the recitation of a numerical range herein includes the numbers at either end of the recited range. In contrast, unless otherwise indicated, recitation of a numerical range "between" two numbers herein does not include the numbers at either end of the recited range. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present specification, including definitions, will control. In addition, the materials, methods, and examples are illustrative only and not intended to be limiting.

I claim:

1. A process for producing formic acid from a carbohydrate-containing material, the process comprising:
    introducing a carbohydrate-containing material to a first reactor;
    hydrolyzing the carbohydrate-containing material in the first reactor in the presence of a mineral acid for a first time period at a first temperature and a first pressure effective to form an intermediate hydrolysate comprising one or more sugars, wherein the mineral acid concentration is about 1 to 10% wt of the contents of the first reactor;
    transferring the intermediate hydrolysate from the first reactor to a second reactor;
    hydrolyzing the intermediate hydrolysate in the second reactor for a second time period at a second temperature less than 195 degrees C. and a second pressure effective to form a hydrolysate product comprising formic acid and levulinic acid; and
    isolating the formic acid in a vapor from the hydrolysate product, wherein the formic acid is produced in an amount that provides a molar ratio of the levulinic acid to the formic acid of at least 0.9.

2. The process of claim 1, wherein the carbohydrate-containing material is hydrolyzed in the first reactor at a first temperature of 190 to 205 degrees C.

3. The process of claim 1, wherein the carbohydrate-containing material is hydrolyzed in the first reactor for a first time period of 10 to 60 seconds.

4. The process of claim 1, wherein the carbohydrate-containing material is hydrolyzed in the first reactor for a first time period of 10 to 60 seconds, at a first temperature of 190 to 205 degrees C., and at a first pressure effective to maintain the intermediate hydrolysate as a liquid; and wherein the mineral acid is present in the first reactor at 2 to 5% wt of the contents of the first reactor.

5. The process of claim 1, wherein the intermediate hydrolysate is hydrolyzed in the second reactor at a second temperature that is lower than the first temperature.

6. The process of claim 1, wherein the intermediate hydrolysate is hydrolyzed in the second reactor at a second temperature of 150 to less than 195 degrees C.

7. The process of claim 1, wherein the intermediate hydrolysate is hydrolyzed in the second reactor for a second time period of 10 to 60 minutes.

8. The process of claim 1, further comprising the step of isolating additional formic acid from a liquid phase of the hydrolysate product obtained from the second reactor by evaporating the formic acid from the liquid phase of the hydrolysate product.

9. The process of claim 4, wherein
    the intermediate hydrolysate is hydrolyzed in the second reactor for a second time period of 10 to 60 minutes; and
    the total formic acid in the outlet streams from the second reactor has a molar ratio of the levulinic acid to the formic acid of at least 0.9.

10. A continuous process for producing formic acid from a carbohydrate-containing material using a first reactor and a second reactor, the process comprising
    continuously supplying the carbohydrate-containing material into the first reactor;
    hydrolyzing the carbohydrate-containing material in the first reactor in the presence of a mineral acid in the first reactor for a first time period of 10 to 60 seconds, at a first temperature of 195 to 235 degrees C. and a first pressure effective to hydrolyze at least a portion of the carbohydrate-containing material to form an intermediate hydrolysate comprising one or more sugars, wherein the mineral acid concentration is about 1 to 10% wt of the contents of the first reactor;
    continuously transferring the intermediate hydrolysate from the first reactor to a second reactor;
    hydrolyzing the intermediate hydrolysate in the second reactor for a second time period that is greater than the first time period, at a second temperature of 170 to less than 195 degrees C. and a second pressure to form a hydrolysate product comprising formic acid and levulinic acid in the second reactor, wherein the second temperature and the second pressure are selected to maintain the intermediate hydrolysate as a liquid in the second reactor; and continuously removing the formic acid in a vapor from the second reactor in an amount that provides a molar ratio of the levulinic acid to the formic acid of at least 0.8.

11. The continuous process of claim 10, wherein the carbohydrate-containing material is hydrolyzed in the first reactor with mineral acid in an amount of 3 to 4.5% wt of the contents of the first reactor, and at first temperature of 205 to 220 degrees C. for a first time period of 10 to 30 seconds.

12. The continuous process of claim 10, wherein the intermediate hydrolysate is hydrolyzed in the second reactor for a second time period of 20 to 35 minutes.

13. The continuous process of claim 10, wherein the second pressure is lower than the first pressure.

14. The continuous process of claim 10, wherein the carbohydrate-containing material consists essentially of cellulose-containing material.

15. A process for producing formic acid from a carbohydrate-containing material, the process comprising:
introducing a carbohydrate-containing material to a first reactor;
hydrolyzing the carbohydrate-containing material in the first reactor in the presence of a mineral acid in an amount of 3.0 to 4.5% wt of the of the contents of the first reactor in the first reactor for a first time period at a first temperature and a first pressure effective to form an intermediate hydrolysate comprising one or more sugars;
transferring the intermediate hydrolysate from the first reactor to a second reactor;
hydrolyzing the intermediate hydrolysate in the second reactor for a second time period at a second temperature of 150 to less than 195 degrees and a second pressure effective to form a hydrolysate product comprising formic acid and levulinic acid; and
isolating the formic acid in a vapor from the hydrolysate product, wherein the formic acid is isolated in an amount that provides a molar ratio of the levulinic acid to the formic acid of at least 0.9.

16. The process of claim 15, wherein the carbohydrate-containing material is hydrolyzed in the first reactor at first temperature of 205 to 220 degrees C. for a first time period of 10 to 30 seconds; and the intermediate hydrolysate is hydrolyzed in the second reactor at second temperature of 170 to less than 195 degrees C. for a second time period of 20 to 35 minutes.

17. The process of claim 15, wherein the carbohydrate-containing material consists essentially of cellulose.

18. A continuous process for producing formic acid from a carbohydrate-containing material using a first reactor and a second reactor, the process comprising
continuously supplying a cellulose-containing material into a first reactor;
hydrolyzing the material in the first reactor in the presence of a mineral acid in an amount of 2 to 5% wt of the cellulose-containing material in the first reactor for a first time period of 10 to 60 seconds, at a first temperature of 195 to 235 degrees C. and at a first pressure effective to maintain the contents of the first reactor in the liquid phase and to hydrolyze at least a portion of the carbohydrate-containing material to form an intermediate hydrolysate comprising one or more sugars and hydroxymethylfurfural;

continuously transferring the intermediate hydrolysate from the first reactor to a second reactor;

hydrolyzing the intermediate hydrolysate in the second reactor for a second time period of 10 to 60 minutes, at a second temperature of 150 to less than 195 degrees C. and a second pressure to form a hydrolysate product comprising formic acid and levulinic acid in the second reactor; wherein the second temperature and the second pressure are selected to maintain the intermediate hydrolysate as a liquid at saturated conditions in the second reactor and the second pressure is less than the first pressure; and continuously removing the formic acid from the second reactor in a vapor; and condensing the formic acid from the vapor, wherein the formic acid is obtained in an amount that provides a molar ratio of the levulinic acid to the formic acid of at least 0.9.

19. The method of claim 1, wherein the yield of formic acid based on carbohydrate is greater than about 55% of the theoretical yield.

20. The method of claim 10, wherein the yield of formic acid based on carbohydrate is greater than about 55% of the theoretical yield.

21. The method of claim 15, wherein the yield of formic acid based on carbohydrate is greater than about 55% of the theoretical yield.

22. The method of claim 18, wherein the yield of formic acid based on carbohydrate is greater than about 55% of the theoretical yield.

23. The method of claim 1, wherein the yield of formic acid based on carbohydrate is greater than about 70% of the theoretical yield.

24. The method of claim 10, wherein the yield of formic acid based on carbohydrate is greater than about 70% of the theoretical yield.

25. The method of claim 15, wherein the yield of formic acid based on carbohydrate is greater than about 70% of the theoretical yield.

26. The method of claim 18, wherein the yield of formic acid based on carbohydrate is greater than about 70% of the theoretical yield.

27. The process of claim 1, wherein the carbohydrate-containing material is hydrolyzed in the first reactor with the mineral acid at 3 to 4.5% wt of the contents of the first reactor.

28. The process of claim 10, wherein the carbohydrate-containing material is hydrolyzed in the first reactor with the mineral acid at 3 to 4.5% wt of the contents of the first reactor.

29. The process of claim 18, wherein the carbohydrate-containing material is hydrolyzed in the first reactor with the mineral acid at 3 to 4.5% wt of the contents of the first reactor.

* * * * *

UNITED STATES PATENT AND TRADEMARK OFFICE
CERTIFICATE OF CORRECTION

| | | |
|---|---|---|
| PATENT NO. | : 8,138,371 B2 | Page 1 of 1 |
| APPLICATION NO. | : 12/401987 | |
| DATED | : March 20, 2012 | |
| INVENTOR(S) | : Stephen W. Fitzpatrick | |

It is certified that error appears in the above-identified patent and that said Letters Patent is hereby corrected as shown below:

On the First Page, right hand column, second line following the heading "OTHER PUBLICATIONS", "5-Hydroxymethyfurfural" should read -- 5-hydroxymethylfurfural --.

On the First Page, right hand column, following the heading "*Primary Examiner*", "Paula" should read -- Paul --.

Signed and Sealed this
Eleventh Day of September, 2012

David J. Kappos
*Director of the United States Patent and Trademark Office*